United States Patent
Miyamoto

(10) Patent No.: US 10,217,230 B2
(45) Date of Patent: Feb. 26, 2019

(54) X-RAY IMAGE PROCESSING APPARATUS, X-RAY IMAGE PROCESSING METHOD, AND STORAGE MEDIUM

(71) Applicant: CANON KABUSHIKI KAISHA, Tokyo (JP)

(72) Inventor: Hideaki Miyamoto, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 28 days.

(21) Appl. No.: 15/140,652

(22) Filed: Apr. 28, 2016

(65) Prior Publication Data

US 2016/0253803 A1    Sep. 1, 2016

Related U.S. Application Data

(63) Continuation of application No. PCT/JP2014/004977, filed on Sep. 29, 2014.

(30) Foreign Application Priority Data

Nov. 13, 2013   (JP) ................................ 2013-235387

(51) Int. Cl.
| | |
|---|---|
| *G06T 7/00* | (2017.01) |
| *G06T 7/30* | (2017.01) |
| *A61B 6/00* | (2006.01) |

(52) U.S. Cl.
CPC ............... *G06T 7/30* (2017.01); *A61B 6/481* (2013.01); *A61B 6/504* (2013.01); *G06T 7/0016* (2013.01);
(Continued)

(58) Field of Classification Search
None
See application file for complete search history.

(56) References Cited

U.S. PATENT DOCUMENTS

| | | | | | |
|---|---|---|---|---|---|
| 4,559,557 | A | * | 12/1985 | Keyes ................. | A61B 6/4042 378/98.11 |
| 5,048,103 | A | * | 9/1991 | Leclerc ................ | G06K 9/4642 378/98.12 |

(Continued)

FOREIGN PATENT DOCUMENTS

| | | |
|---|---|---|
| JP | 2006-187511 A | 7/2006 |
| JP | 2007-215930 A | 8/2007 |

(Continued)

OTHER PUBLICATIONS

Eiho, Sigeru, and Ying Qian. "Detection of coronary artery tree using morphological operator." Computers in Cardiology 1997. IEEE, 1997.*

(Continued)

*Primary Examiner* — Vu Le
*Assistant Examiner* — Tracy Mangialaschi
(74) *Attorney, Agent, or Firm* — Venable LLP

(57) ABSTRACT

An X-ray image processing apparatus includes a first difference processing unit for generating a first difference image by performing difference processing between a mask image obtained by capturing an object before an inflow of a contrast medium and a live image after the inflow of the contrast medium, a first obtaining processing unit for obtaining a line-shaped region indicating a region, into which the contrast medium has flowed, using a distribution of pixel values in the first difference image, a second obtaining processing unit for obtaining a peripheral region of the line-shaped region from the first difference image using pixel values of pixels adjacent to the line-shaped region, and a registration processing unit for performing registration between pixels of the live image and the mask image by comparing positions using the line-shaped region and the peripheral region.

26 Claims, 9 Drawing Sheets

(52) U.S. Cl.
CPC ............ *G06T 2207/10116* (2013.01); *G06T 2207/20224* (2013.01); *G06T 2207/30101* (2013.01)

(56) References Cited

U.S. PATENT DOCUMENTS

| | | | |
|---|---|---|---|
| 8,175,357 B2 | 5/2012 | Ozawa | 382/130 |
| 8,467,498 B2 | 6/2013 | Ohishi | 378/98.12 |
| 8,488,853 B2 | 7/2013 | Sato et al. | 382/128 |
| 8,542,794 B2 | 9/2013 | Miyamoto | 378/62 |
| 8,798,352 B2 | 8/2014 | Miyamoto | 382/132 |
| 9,275,439 B2 | 3/2016 | Miyamoto | 382/132 |
| 2001/0021263 A1* | 9/2001 | Oosawa | G06T 5/50 382/132 |
| 2007/0036405 A1* | 2/2007 | Lienard | G06T 5/50 382/128 |
| 2007/0104317 A1* | 5/2007 | Ohishi | A61B 6/504 378/98.12 |
| 2007/0140427 A1* | 6/2007 | Jensen | A61B 6/481 378/98.12 |
| 2008/0037845 A1* | 2/2008 | Deuerling-Zheng | G06T 7/238 382/130 |
| 2013/0294674 A1 | 11/2013 | Miyamoto | 382/132 |
| 2016/0117809 A1 | 4/2016 | Miyamoto | 382/132 |

FOREIGN PATENT DOCUMENTS

| | | |
|---|---|---|
| JP | 2008-212241 A | 9/2008 |
| JP | 2011-245158 A | 12/2011 |
| WO | WO 9418639 A1 * | 8/1994 ............ G06T 5/50 |

OTHER PUBLICATIONS

Bentoutou, Y., et al. "An invariant approach for image registration in digital subtraction angiography." Pattern Recognition 35.12 (2002): 2853-2865.*

* cited by examiner

INTER-IMAGE DIFFERENCE PROCESSING

OBTAINING OF CONTRASTED VASCULAR REGION

X-RAY IMAGE PROCESSING APPARATUS, X-RAY IMAGE PROCESSING METHOD, AND STORAGE MEDIUM

This application is a continuation of International Patent Application No. PCT/JP2014/004977 filed on Sep. 29, 2014, and claims priority to Japanese Patent Application No. 2013-235387 filed on Nov. 13, 2013, the entire content of both of which is incorporated herein by reference.

TECHNICAL FIELD

The present invention relates to an X-ray image processing apparatus, an X-ray image processing method, and a storage medium.

BACKGROUND ART

With recent advances in the digital technology, it has become popular to perform digital processing for images even in the medical field. A preferred application example of digital image processing is DSA processing of obtaining digital subtraction angiography (to be referred to as DSA hereinafter). A DSA image is an image obtained by obtaining images before and after the inflow of a contrast medium into an object, and subtracting an image (mask image) before the inflow of the contrast medium from an image (live image) after the inflow of the contrast medium. In the inter-image difference processing of subtracting the mask image from the live image, a vascular region serving as a region of interest in diagnosis is obtained as a change region between the images that is generated by the inflow of the contrast medium. Furthermore, in the inter-image difference processing, a region except for the vascular region serving as a region of interest is removed as a background region. The thus generated DSA image is an image useful for diagnosis because the vascular region serving as a region of interest can be observed without any influence of an object structure.

The purpose of using a DSA image for diagnosis is clear depiction of a contrasted vascular image. This purpose is achieved by subtracting a mask image from a live image. Since, however, an object generally moves, a motion artifact unwantedly appears in a DSA image. In a DSA image expected to ideally depict only a vascular region into which a contrast medium has flowed, a motion artifact interferes with clear depiction of a vascular image. Especially if a motion artifact occurs in a vascular region, angiostenosis or the like becomes very difficult to see.

To solve this problem, PTL 1 discloses a method of setting, particularly based on a motion artifact, a region of interest in a subtraction image obtained by subtracting a mask image from a live image, and performing registration by pixel shifting within the region of interest. Registration by pixel shifting is a method of reducing a motion artifact by shifting, upward, downward, rightward, or leftward, pixels to be subtracted when performing inter-image difference processing between a live image and a mask image. In this method, a motion artifact is automatically, effectively reduced by calculating a pixel shift amount from a region of interest set based on the motion artifact.

CITATION LIST

Patent Literature

PTL 1: Japanese Patent Laid-Open No. 2007-215930

SUMMARY OF THE INVENTION

Technical Problem

It is difficult to perform complete registration processing for a DSA image. Since an object moves three-dimensionally, it is theoretically impossible to perform registration by two-dimensional processing such as pixel shifting. A method which uses non-rigid body registration is considered to cope with three-dimensional motion. However, the algorithm becomes complicated to greatly increase the calculation cost. In addition, in some cases, a false image which does not exist in an actual object may be generated.

To solve this problem, like PTL 1, a method of performing partial optimization by executing registration within a region set based on a motion artifact is considered. If partial optimization is performed, it is possible to suppress the calculation cost by performing registration in a particularly necessary portion instead of performing registration in an entire image.

For a DSA image, it is desirable to perform registration in a contrasted vascular region serving as a region of clinical interest. However, the main purpose of the method described in PTL 1 is to reduce a motion artifact, and does not consider setting a region of clinical interest as a region of interest.

The present invention provides an X-ray image processing technique capable of performing registration between a live image and a mask image using a contrasted vascular region of clinical interest and its peripheral region in registration processing for a DSA image.

Solution to Problem

According to one aspect of the present invention, there is provided an X-ray image processing apparatus comprising: a first difference processing unit configured to generate a first difference image by performing difference processing between a mask image obtained by capturing an object before an inflow of a contrast medium and a live image after the inflow of the contrast medium; a first obtaining processing unit configured to obtain a line-shaped region indicating a region, into which the contrast medium has flowed, using a distribution of pixel values in the first difference image; a second obtaining processing unit configured to obtain a peripheral region of the line-shaped region from the first difference image using pixel values of pixels adjacent to the line-shaped region; and a registration processing unit configured to perform registration between pixels of the live image and the mask image by comparing positions using the line-shaped region and the peripheral region.

Advantageous Effects of Invention

According to the present invention, it is possible to perform registration between a live image and a mask image using a contrasted vascular region of clinical interest and its peripheral region in registration processing for a DSA image. It is possible to perform registration between the live image and the mask image by reducing the influence of a motion artifact in the DSA image.

Other features and advantages of the present invention will be apparent from the following description taken in conjunction with the accompanying drawings. Note that the same reference numerals denote the same or like components throughout the accompanying drawings.

BRIEF DESCRIPTION OF THE DRAWINGS

The accompanying drawings, which are incorporated in and constitute a part of the specification, illustrate exemplary embodiments of the invention and, together with the description, serve to explain the principles of the present invention.

DESCRIPTION OF THE EMBODIMENTS

Embodiments of the present invention will be exemplarily described in detail below with reference to the accompanying drawings. Note that components to be described in these embodiments are merely examples. The technical scope of the present invention is defined by the scope of the claims, and is not limited by the following embodiments.

First Embodiment

Figure 1:
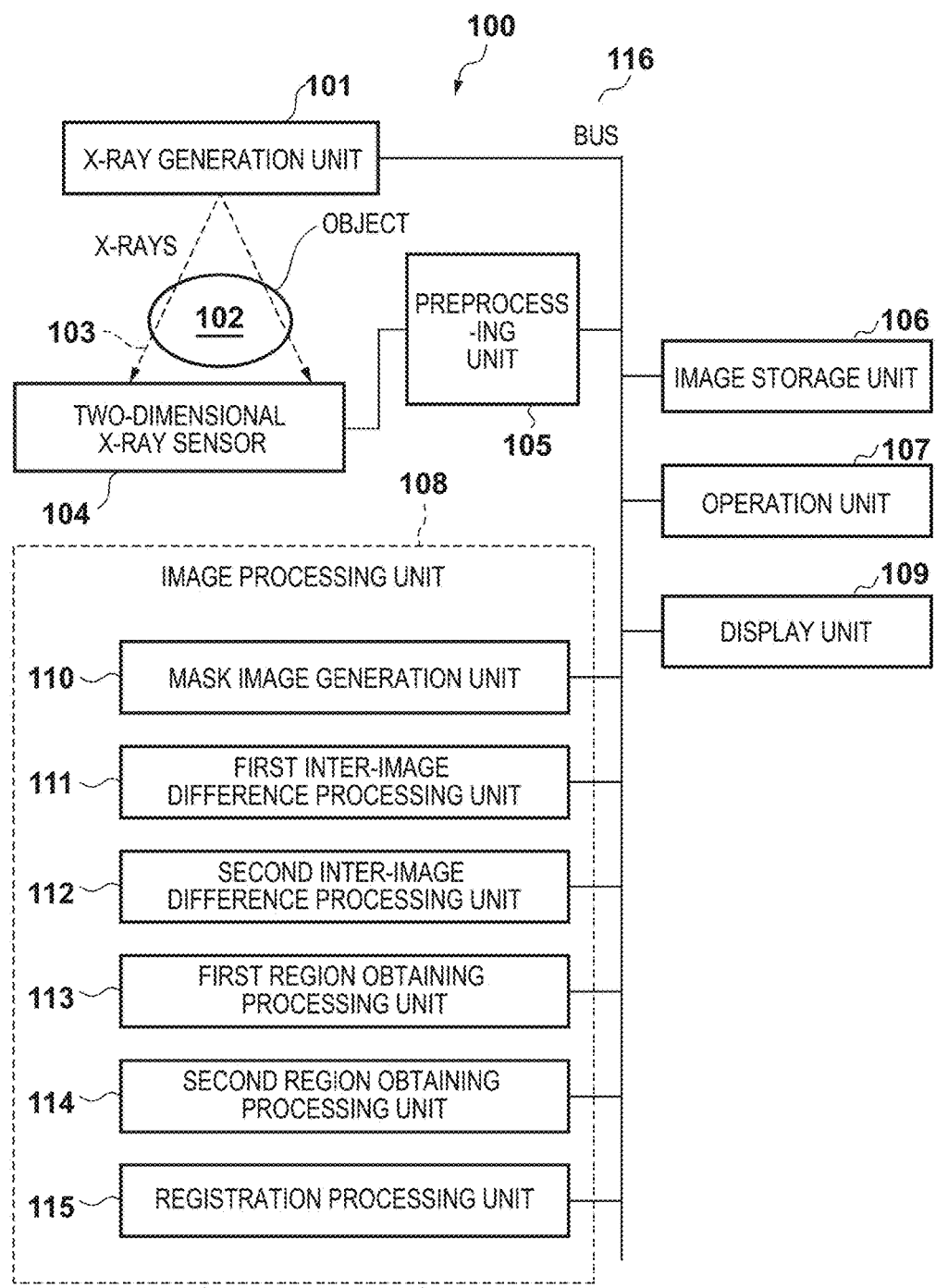
FIG. 1 is a block diagram for explaining an X-ray image processing apparatus according to the first and second embodiments.

FIG. 1 is a block diagram showing the schematic arrangement of an image processing apparatus (to be referred to as an "X-ray image processing apparatus 100" hereinafter) according to the embodiment. The X-ray image processing apparatus 100 includes an X-ray generation unit 101, a two-dimensional X-ray sensor 104, a preprocessing unit 105, an image storage unit 106, an operation unit 107, an image processing unit 108, and a display unit 109.

The X-ray generation unit 101 can generate X-ray pulses of 3 to 30 pulses per sec. The two-dimensional X-ray sensor 104 receives X-rays 103 having passed through an object 102, and captures, as an X-ray image, a moving image synchronized with X-ray pulses. The two-dimensional X-ray sensor 104 functions as an image capturing unit which captures a moving image of the object 102 irradiated with X-rays. The preprocessing unit 105 performs preprocessing for the respective frames of the moving image captured by the two-dimensional X-ray sensor 104 at different timings.

The image processing unit 108 performs image processing for the captured X-ray image. The operation unit 107 is used to input an operation instruction from a user. The display unit 109 displays the X-ray image. The image storage unit 106 stores the moving image preprocessed by the preprocessing unit 105 and the X-ray image having undergone the image processing by the image processing unit 108.

Furthermore, the image processing unit 108 includes a mask image generation unit 110, a first inter-image difference processing unit 111, a second inter-image difference processing unit 112, a first region obtaining processing unit 113, a second region obtaining processing unit 114, and a registration processing unit 115.

The X-ray generation unit 101, two-dimensional X-ray sensor 104, preprocessing unit 105, image storage unit 106, image processing unit 108, operation unit 107, and display unit 109 are connected via a bus 116.

This embodiment will describe a case in which the above-described X-ray image processing apparatus 100 captures (to be referred to as X-ray moving image capturing hereinafter) the flow of a contrast medium in blood vessels. The X-ray image processing apparatus 100 starts X-ray moving image capturing by receiving a capturing start instruction from the user via the operation unit 107. The user sets capturing conditions via the operation unit 107 so as to obtain desired image quality. The capturing conditions set via the operation unit 107 are reflected to the capturing start instruction output from the operation unit 107.

If the capturing start instruction is input, the X-ray generation unit 101 generates X-ray pulses according to the capturing conditions set by the user.

The two-dimensional X-ray sensor 104 generates frames of an X-ray image one by one in synchronism with the X-ray pulses, and outputs the generated frames to the preprocessing unit 105. The preprocessing unit 105 performs, for each frame of the X-ray image, predetermined preprocessing in consideration of the characteristics of the two-dimensional X-ray sensor 104.

If it is necessary to reproduce the image after capturing, the image storage unit 106 saves the X-ray image in accordance with a saving instruction received from the user via the operation unit 107.

When performing digital subtraction angiography (DSA processing) in X-ray moving image capturing, the preprocessing unit 105 inputs the X-ray image having undergone the preprocessing to the mask image generation unit 110. An image (to be referred to as a mask image hereinafter) before the inflow of the contrast medium generally includes a few frames immediately after the start of X-ray moving image capturing and, more preferably, includes a frame immediately before the inflow of the contrast medium, which has small misregistration with respect to an image (to be referred to as a live image hereinafter) after the inflow of the contrast medium. A few frames after the start of X-ray moving image capturing are used to generate a mask image. If the user presets, via the operation unit 107, a frame number (for example, a condition such as a frame number after the start of X-ray moving image capturing) to be used as a mask image, the mask image generation unit 110 outputs, as a mask image, a frame satisfying the condition to the image storage unit 106 in accordance with the setting.

Alternatively, it may be configured so that the mask image generation unit 110 detects the inflow of a contrast medium by analyzing frames obtained by X-ray moving image capturing, and automatically selects a frame immediately before the inflow of the contrast medium.

The mask image generation unit 110 may add pixel values I of a plurality of frames, and output the resultant data as a mask image M, as given by:

$$M(x, y) = \frac{1}{endNo - startNo + 1} \sum_{n=startNo}^{endNo} I_n(x, y) \quad (1)$$

where n represents a frame number of an image to be output by the two-dimensional X-ray sensor 104, and In represents an image of the nth frame. Parameters startNo and endNo in equation (1) respectively indicate the start frame number and end frame number of frame addition which are designated in advance by the user. Furthermore, (x, y) represent the pixel index of an image, In(x, y) represents a pixel value at the coordinates (x, y) on the image I of the nth frame, and M(x, y) represents a pixel value at the coordinates (x, y) on the mask image M.

The mask image generation unit 110 outputs the generated mask image, and the image storage unit 106 saves the mask image generated by the mask image generation unit 110. Frames captured before and during creation of the mask image can be displayed on the display unit 109 in real time after undergoing predetermined image processing (not shown) for display.

The X-ray image processing apparatus 100 performs, for each frame of the image (live image) after the inflow of the contrast medium, which has been captured after the creation of the mask image, DSA image generation processing as processing for generating a DSA image by inter-image difference processing using the mask image saved in the image storage unit 106. The procedure of the DSA image generation processing will be described below.

(DSA Image Generation Processing)

Figure 2:
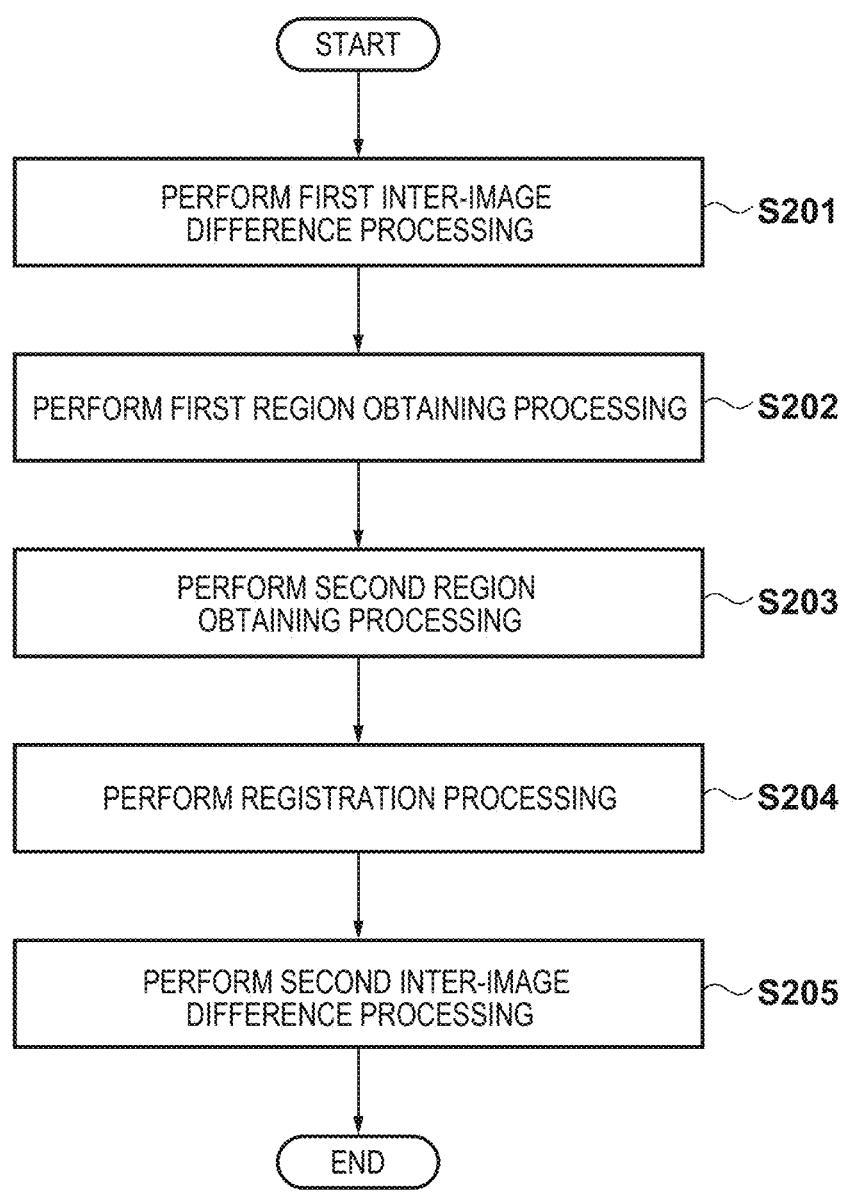
FIG. 2 is a flowchart for explaining a processing procedure according to the first embodiment.
Figure 7A:
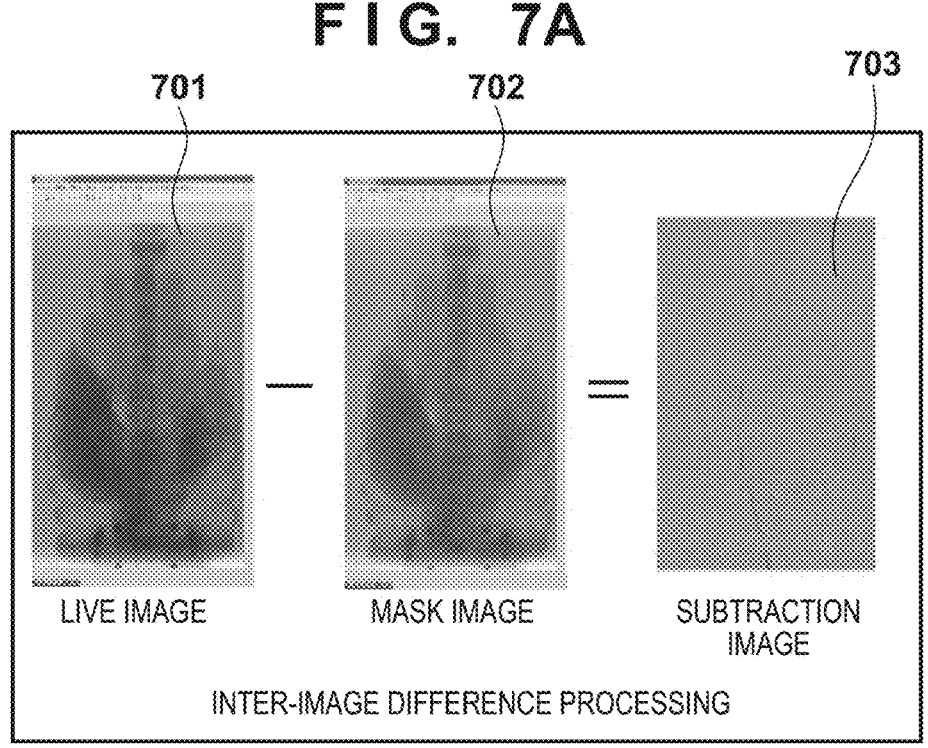
FIG. 7A is a view exemplarily showing inter-image difference processing by a first inter-image difference processing unit.

FIG. 2 is a flowchart for explaining the procedure of the DSA image generation processing. In step S201, the first inter-image difference processing unit 111 generates a first subtraction image (difference image) by performing inter-image difference processing between the live image as the image preprocessed by the preprocessing unit 105 and the mask image saved in the image storage unit 106 by:

$$S1(x,y) = L(x,y) - M(x,y) \quad (2)$$

where S1 represents the first subtraction image (difference image), L represents the live image, and M represents the mask image. Furthermore, (x, y) represent the pixel index of an image, and S1(x, y), L(x, y), and M (x, y) respectively represent the pixel values of the first subtraction image, live image, and mask image. FIG. 7A is a view exemplarily showing inter-image difference processing by the first inter-image difference processing unit 111, in which a live image 701 corresponds to L (to be also referred to as the live image L hereinafter) in equation (2), and a mask image 702 corresponds to M (to be also referred to as the mask image M hereinafter) in equation (2). A subtraction image 703 (difference image) obtained by the inter-image difference processing corresponds to S1 in equation (2).

Figure 3:
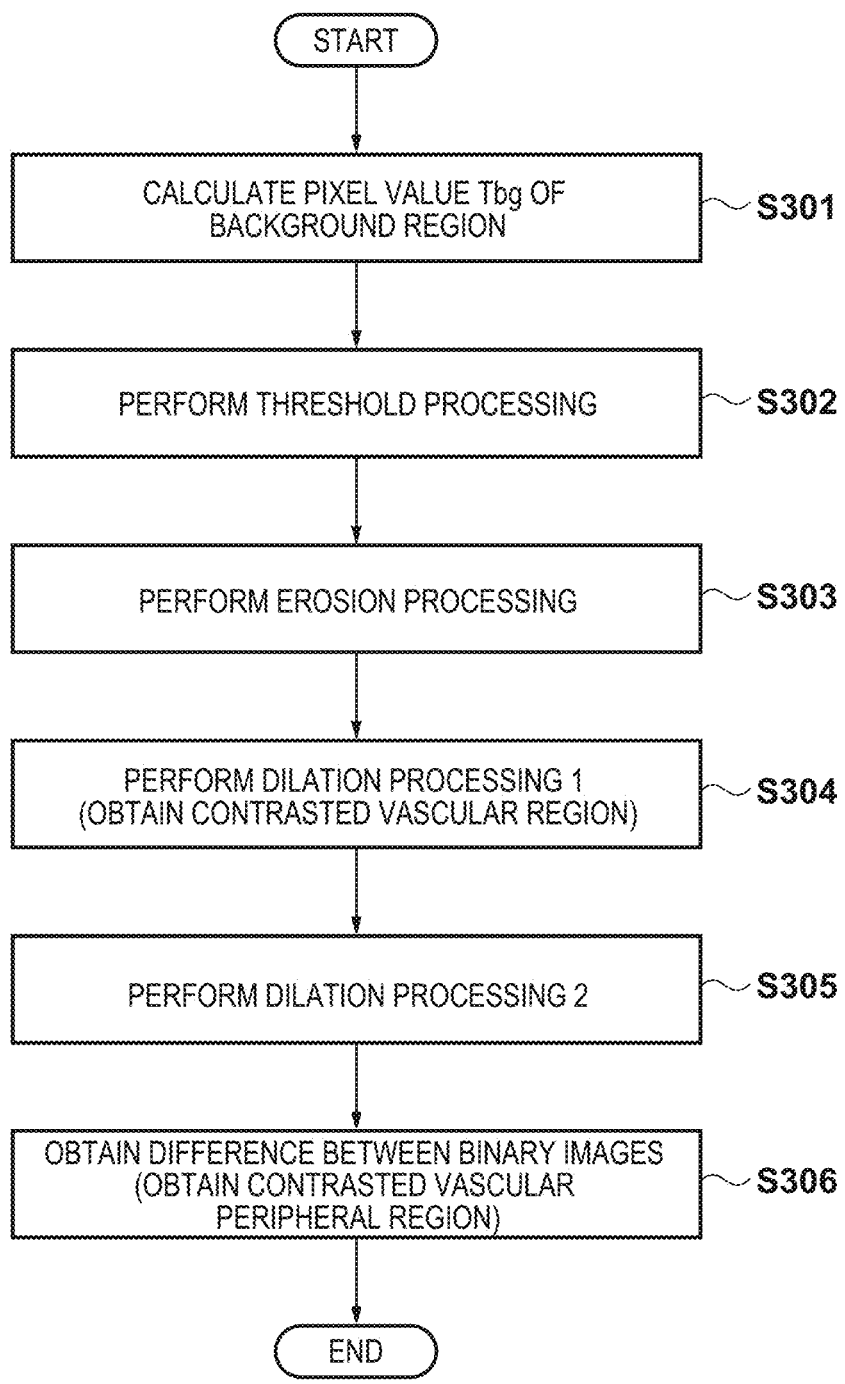
FIG. 3 is a flowchart for explaining the procedure of an example of region obtaining processing according to the first embodiment.
Figure 7B:
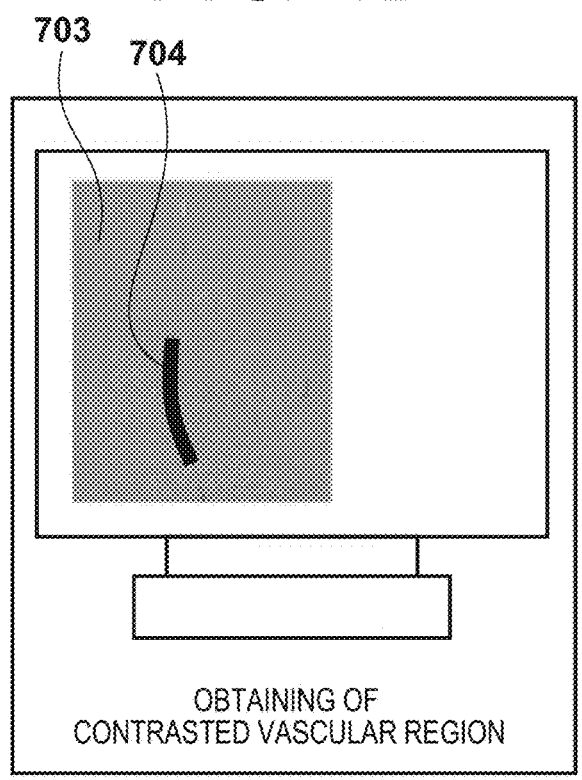
FIG. 7B is a view exemplarily showing the inter-image difference processing by the first inter-image difference processing unit.

In step S202, using the distribution of the pixel values in the first subtraction image S1 (difference image), the first region obtaining processing unit 113 obtains a vascular region (contrasted vascular region) into which the contrast medium has flowed. The vascular region (contrasted vascular region) is obtained as a line-shaped region from the first subtraction image S1 (difference image). FIG. 7B is a view exemplarily showing, as a vascular region (contrasted vascular region), a line-shaped region indicating a region into which the contrast medium has flowed. The first region obtaining processing unit 113 obtains a line-shaped region 704 in the subtraction image 703 (difference image) serving as the first subtraction image. The detailed contents of the processing of obtaining the line-shaped region 704 in this step will be described later with reference to FIG. 3.

In step S203, the second region obtaining processing unit 114 obtains the peripheral region (contrasted vascular peripheral region) of the line-shaped region using the first subtraction image S1 and the pixel values of pixels adjacent to the line-shaped region 704 (contrasted vascular region) indicating the region into which the contrast medium has flowed. The detailed contents of the obtaining processing in this step will be described later with reference to FIG. 3.

In step S204, the registration processing unit 115 compares positions using the line-shaped region (contrasted vascular region) and the peripheral region (contrasted vascular peripheral region) of the line-shaped region. The registration processing unit 115 obtains, by comparing the positions, a correction amount which minimizes misregistration between pixels (pixel sets) in the live image L and mask image M, and performs registration between the live image L and the mask image M.

Figure 8A:
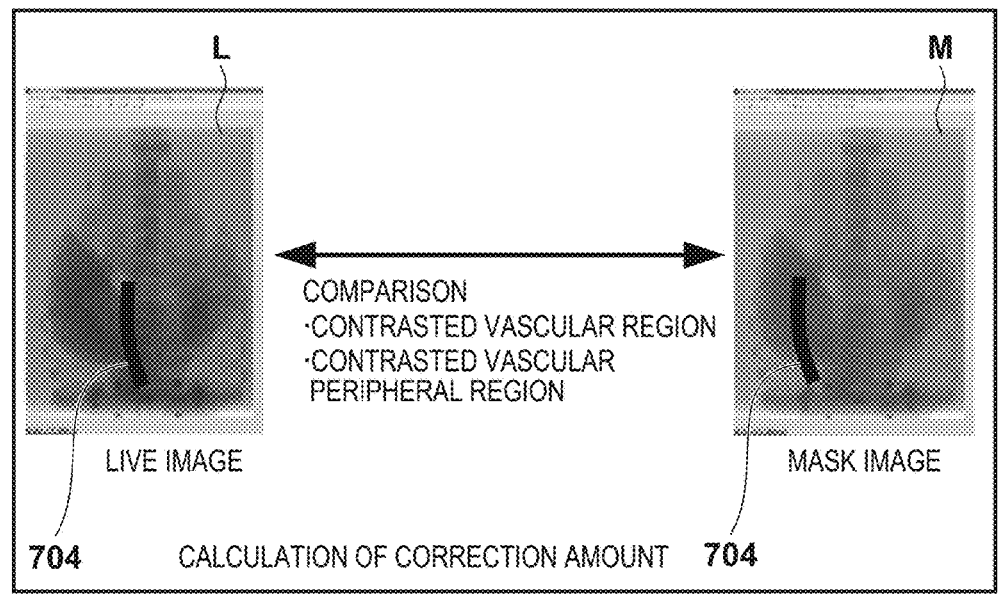
FIG. 8A is a view exemplarily showing registration processing.

FIG. 8A is a view exemplarily showing correction amount calculation processing by the registration processing unit 115. The registration processing unit 115 obtains a correction amount which minimizes misregistration between corresponding pixels in the live image L and mask image M by comparing positions using the obtained line-shaped region (contrasted vascular region) and the peripheral region (contrasted vascular peripheral region). The registration processing unit 115 performs registration between the live image L and the mask image M using the obtained correction amount.

Figure 8B:
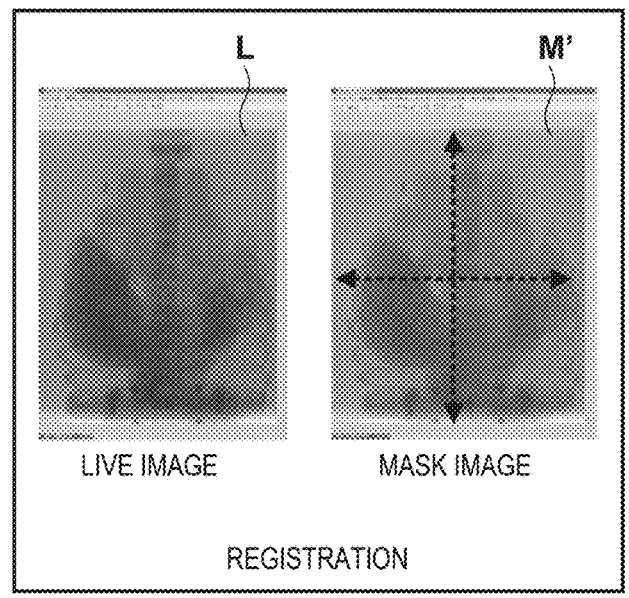
FIG. 8B is a view exemplarily showing registration processing.

As the registration processing, for example, the registration processing unit 115 registers the live image with the mask image with reference to the mask image. As the registration processing, for example, the registration processing unit 115 registers the mask image with the live image with reference to the live image. Alternatively, the registration processing unit 115 may perform registration between the live image and the mask image by deforming both the images. For the sake of descriptive simplicity, this embodiment will describe a case in which a registered mask image M' is obtained by registering the mask image M with the live image L with reference to the live image L, and output from the registration processing unit 115. FIG. 8B is a view exemplarily showing the registration processing by the registration processing unit 115, in which the mask image L undergoes registration according to comparison of the positions in the line-shaped region and the peripheral region based on the correction amount calculated by the correction amount calculation processing.

Figure 9A:
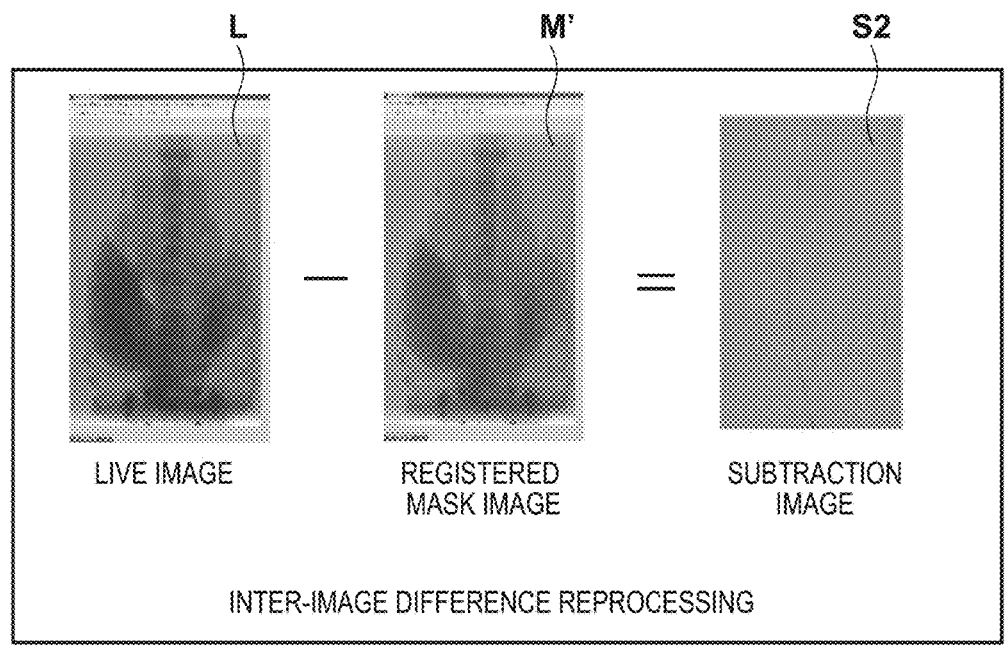
FIG. 9A is a view exemplarily showing inter-image difference processing by a second inter-image difference processing unit.
Figure 9B:
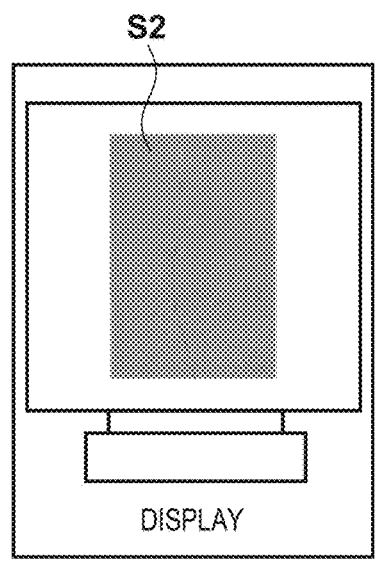
FIG. 9B is a view exemplarily showing the inter-image difference processing by the second inter-image difference processing unit.

In step S205, the second inter-image difference processing unit 112 generates a second subtraction image by subtracting the registered mask image M' from the live image L, and outputs the generated image. The X-ray image processing apparatus 100 inputs the second subtraction image as a DSA image to the display unit 109, and the display unit 109 displays the DSA image. FIG. 9A is a view exemplarily showing inter-image difference processing by the second inter-image difference processing unit 112, and shows a case in which a second subtraction image (S2) is generated by subtracting the registered mask image M' from the live image L. FIG. 9B is a view exemplarily showing the second subtraction image (DSA image: S2) obtained by the inter-image difference processing by the second inter-image difference processing unit 112.

(Obtaining of Contracted Vascular Region and Contrasted Vascular Peripheral Region)

The processing of obtaining the contrasted vascular region and contrasted vascular peripheral region will be described in detail next. Various methods can be used to obtain the contrasted vascular region in step S202 and obtain the contrasted vascular peripheral region in step S203. In this embodiment, a method which uses threshold processing and a morphological operation will be described with reference to a flowchart shown in FIG. 3.

In step S301, the first region obtaining processing unit 113 calculates a pixel value Tbg of a background region in the first subtraction image. In an ideal state in which the live image L and the mask image M are obtained with the same X-ray dose, the pixel value Tbg of the background region is 0 (zero). In fact, however, an X-ray dose at the time of capturing the live image L is different from that at the time of capturing the mask image M due to variations in X-rays, and thus the pixel value Tbg of the background region may not be zero. The first region obtaining processing unit 113 converts pixel values in the first subtraction image into a histogram using the fact that the background region occupies a large area of the entire first subtraction image. The first region obtaining processing unit 113 calculates, as the pixel value (background pixel value) Tbg of the background region, the pixel value serving as a mode.

In step S302, the first region obtaining processing unit 113 performs, for the first subtraction image, threshold processing using the pixel value Tbg of the background region as a threshold, and outputs a binary image in which the contrasted vascular region is represented by "1" and the remaining background region is represented by "0". In the first subtraction image, using the fact that the contrasted vascular region is generally a region having pixel values smaller than the pixel value Tbg of the background region, the contrasted vascular region is obtained (roughly obtained) by the threshold processing given by:

$$B0(x, y) = \begin{cases} 1 & S1(x, y) < Tbg \\ 0 & \text{otherwise} \end{cases} \quad (3)$$

where S1 represents the first subtraction image, B0 represents the binary image as a result of the threshold processing, and (x, y) represent coordinates on the image. Furthermore, S1(x, y) represents the pixel value of the pixel (x, y) of the first subtraction image S1, and B0(x, y) represents the pixel value of the pixel (x, y) of the binary image B0. Therefore, the first region obtaining processing unit 113 performs, for all the pixels, comparison processing of comparing the pixel value S1(x, y) of the first subtraction image S1 with the pixel value Tbg (threshold) of the background region in accordance with equation (3), thereby obtaining the binary image B0. Note that since noise generally exists in the X-ray image, the contrasted vascular region (line-shaped region) may not be clearly divided by the above-described threshold. To void the influence of noise and obtain only a vascular region in which the contrast medium is dense, the first region obtaining processing unit 113 can perform, using an offset value offset larger than zero, threshold processing given by:

$$B0(x, y) = \begin{cases} 1 & S1(x, y) < Tbg - \text{offset} \\ 0 & \text{otherwise} \end{cases} \quad (4)$$

In step S303, the first region obtaining processing unit 113 applies the erosion processing of the morphological operation to the binary image B0 a predetermined number of times, and outputs an eroded binary image B1 (erosion processing). This processing replaces a pixel (1-pixel) indicating "1" isolated on the binary image B0 by a pixel (0-pixel) indicating "0", thereby obtaining the effect of reducing noise. Since the number of times of application of the erosion processing depends on an image resolution, the capturing conditions, and the pixel value Tbg (threshold) of the background region, an experimentally determined appropriate number is set. If it is not necessary to reduce noise, this step can be skipped.

In step S304, the first region obtaining processing unit 113 applies the dilation processing of the morphological operation to the binary image B0 or the eroded binary image B1 a predetermined number of times, and outputs a binary image B2 having undergone the dilation processing (dilation processing 1). This processing is processing of replacing, by a "1-pixel", a "0-pixel" (a pixel indicating the background) adjacent to a "1-pixel" (a pixel indicating the contrasted vascular region (line-shaped region)) in the image B1. This produces an effect of connecting the contrasted vascular region which should originally be connected, and has been generated by the above-described threshold processing or erosion processing, or misregistration between the live image L and the mask image M. The number of times of application of the dilation processing depends on the image resolution, the capturing conditions, the pixel value Tbg (threshold) of the background region, and the above-described number of times of application of the erosion processing. If a desired contrasted vascular region is only the central portion of a thick blood vessel or a region in which the contrast medium is dense, the number of times of application of the dilation processing may be decreased or the dilation processing may be skipped. The above processing is processing performed by the first region obtaining processing unit 113, and the "1-pixels" of the obtained binary image B2 indicate the contrasted vascular region (line-shaped region).

In step S305, the second region obtaining processing unit 114 performs dilation processing using, as an initial image, the binary image B2 serving as the contrasted vascular region, thereby obtaining a binary image B3 in which "1-pixels" indicate the contrasted vascular peripheral region (dilation processing 2). As the number of times of application of the dilation processing, an appropriate number is determined in consideration of the image resolution and the size of the desired contrasted vascular peripheral region.

In step S306, the second region obtaining processing unit 114 obtains a binary image B4, in which only the contrasted vascular peripheral region includes "1-pixels", by subtracting the binary image B2 from the binary image B3 to exclude the contrasted vascular region (inter-binary image difference processing) by:

$$B4(x,y) = B3(x,y) - B2(x,y) \quad (5)$$

The processing executed by the second region obtaining processing unit 114 has been explained, and the "1-pixels" of the obtained binary image B4 indicate the contrasted vascular peripheral region.

Instead of the above-described method, the contrasted vascular region may be defined as a connected region, a binary image obtained by the threshold processing may be labeled, and a region having a largest area or a region having a line-shaped structure may be obtained as the contrasted vascular region. Alternatively, using the fact that a subtraction image (difference image) as a region obtaining target is a moving image, a contrasted vascular region may be obtained for the first frame by the above-described threshold processing and morphological operation, and obtaining processing may be performed for each of the second frame and subsequent frames based on a result of obtaining a preceding frame. More specifically, it is possible to use a method of setting, as a start region, the contrasted vascular region obtained in the preceding frame, and obtaining, by the threshold and dilation processing, a region which can be considered as a contrasted blood vessel in a neighboring region.

(Registration Processing)

The registration processing in step S204 of FIG. 2 will be described next. In this embodiment, the registration processing in step S204 can use various methods. A method will now be described, in which registration with the live image L is performed by shifting the pixels of the mask image M (pixel shifting) based on the binary image B2 representing the above-described contrasted vascular region and the binary image B4 representing the contrasted vascular peripheral region.

Letting i be a shift amount in the x-axis direction and j be a shift amount in the y-axis direction, the image M' obtained by performing pixel shifting for the mask image M can be given by:

$$M'(x, y) = \begin{cases} M(x-i, y-j) & 0 \leq x-i < W, 0 \leq y-j < H \\ \text{dummy} & \text{otherwise} \end{cases} \quad (6)$$

where W and H respectively represent the horizontal and vertical sizes of the mask image M and image M'. If coordinates (x−i, y−j) fall outside the mask image M, there is no pixel value, and thus a predetermined arbitrary value dummy is set as the value of M' (x, y).

The registration processing using pixel shifting for shifting pixels is processing of generating the image M' while changing the shift amount (i, j) within a predetermined shift range, and obtaining the shift amount (i, j) as a correction amount which minimizes misregistration by comparing the image M' with the live image L. The maximum shift amount is represented by smax, and the shift range is represented by (−smax≤i≤smax, −smax≤j≤smax). Letting E(i, j) be the evaluation value of misregistration between the live image L when the shift amount is (i, j) and the image M' having undergone pixel shifting, the evaluation value E (evaluation function) can be obtained by:

$$E(i, j) = \sum_{x=smax}^{W-1-smax} \sum_{y=smax}^{H-1-smax} [aB2(x, y) + bB4(x, y)][M'(x, y) - L(x, y)]^2 \quad (7)$$

$$= \sum_{x=smax}^{W-1-smax} \sum_{y=smax}^{H-1-smax} \begin{bmatrix} aB2(x, y) + \\ bB4(x, y) \end{bmatrix} [M(x-i, y-j) - L(x, y)]^2$$

The image M' obtained by performing pixel shifting for the mask image M by the shift amount (i, j) which minimizes the evaluation value E is the registered mask image output from the registration processing unit 115 in step S204. Equation (7) indicates an operation of multiplying, by coefficients a and b respectively indicating predetermined weighting coefficients within regions represented by the binary images B2 and B4, a value obtained by squaring the difference in pixel value between the live image L and the mask image M' having undergone pixel shifting, and totalizing the results. By totalizing the values within a range obtained by considering the maximum shift amount smax, a variation in total number of pixels caused by the shift amount and the value dummy are prevented from influencing the evaluation value E.

Note that a and b represent the coefficients each for determining the degree of contribution to the evaluation value of the region represented by the binary image B2 or B4. The reason why the degrees a and b of contribution are set as different weighting coefficients for the binary images B2 and B4 is that it is considered that the contrasted vascular region represented by the binary image B2 and the contrasted vascular region peripheral region represented by the binary image B4 have different characteristics. That is, in the contrasted vascular peripheral region represented by the binary image B4, the evaluation value becomes zero by the shift amount by which ideal registration is performed since no contrasted vascular region exists in the live image and no contrasted vascular region exists either in the mask image. On the other hand, in the contrasted vascular region represented by the binary image B2, the evaluation value given by equation (7) based on comparison of pixel values does not become zero since the contrasted vascular region exists in the live image and no contrasted vascular region exists in the mask image. Therefore, by setting the degrees of contribution to satisfy a<b, a more preferable evaluation value can be obtained by:

$$E(i, j) = \sum_{x=smax}^{W-1-smax} \sum_{y=smax}^{H-1-smax} \begin{bmatrix} B2(x, y)f(M'(x, y), L(x, y)) + \\ B4(x, y)g(M'(x, y), L(x, y)) \end{bmatrix} \quad (8)$$

$$= \sum_{x=smax}^{W-1-smax} \sum_{y=smax}^{H-1-smax} \begin{bmatrix} B2(x, y)f(M(x-i, y-j), L(x, y)) + \\ B4(x, y)g(M(x-i, y-j), L(x, y)) \end{bmatrix}$$

As indicated by equation (8), the evaluation value may be obtained using functions f and g for the binary images B2 and B4, respectively. For example, with respect to the contrasted vascular peripheral region represented by the binary image B4, the function g is defined to calculate the evaluation value based on the pixel values like equation (7). On the other hand, with respect to the contrast vascular region represented by the binary image B2, the function f is defined to compare edges in order to compare structures in blood vessels, instead of the pixel values which consider the presence/absence of the contrast medium. The registration processing unit 115 can perform edge detection processing for the live image L and the mask image M, and compare obtained pieces of edge information, thereby performing registration between the live image L and the mask image M. For example, the function f can be given by:

$$f(M'(x,y), L(x,y)) = \{M'(x+1,y) - M'(x-1,y)\} - \{L(x+1,y) - L(x-1,y)\} + \{M'(x,y+1) - M'(x,y-1)\} - \{L(x,y+1) - L(x,y-1)\} \quad (9)$$

Equation (9) is used to obtain derivative values in the horizontal and vertical directions at the pixels (x, y) of interest of the mask image M' and live image L, and set them as evaluation values.

(Generation of Second Subtraction Image)

The processing of generating the second subtraction image, which has been explained in step S205, will be described. The second inter-image difference processing unit 112 generates the second subtraction image S2 by subtracting the registered mask image M' from the live image L (equation (10)). At this time, a pixel (x−i<0, x−i≥W, y−j<0, y−j≥H) having the value dummy in the registered mask image M' has the value dummy also in the second subtraction image.

$$S2(x, y) = \begin{cases} L(x, y) - M'(x, y) & 0 \le x - i < W, 0 \le y - j < H \\ \text{dummy} & \text{otherwise} \end{cases} \quad (10)$$

A case in which pixel shifting is used as a registration method has been explained above. However, the registration method is not limited to the method which uses pixel shifting. For example, parametric image deformation such as rotation, enlargement, or reduction may be used depending on the movement of the object during a period from generation of the mask image to capturing of the live image. Alternatively, non-rigid body registration such as warping for arranging control points in a mesh shape in each of the mask image and the live image, obtaining the correspondence between the mask image and the live image at each control point, and performing movement of the control points and interpolation of a pixel value between the control points may be used. The registration processing unit 115 divides each of the mask image M and the live image L into a plurality of meshes, and associates control points indicating nodes of the meshes between the mask image M and the live image L. The registration processing unit 115 can perform registration between the mask image and the live image by the non-rigid body registration processing using the movement amounts of the control points and a value interpolated between the control points based on the movement amounts for the positions of the meshes other than the control points. The registration processing unit 115 obtains, as correction amounts, the movement amounts of corresponding positions between the mask image and the live image and the movement amount interpolated between the corresponding positions by the non-rigid body registration processing using a result of comparing position of the line-shaped region with that of the peripheral region. Based on the obtained correction amounts, the registration processing unit 115 can perform registration between the live image and the mask image.

The method of generating one mask image in the mask image generation unit 110 and registering it with a live image has been explained above. However, a plurality of mask images may be generated in advance, and a mask image which has smallest misregistration may be selected instead of registration with the live image. That is, if N masks Mn (n=1, . . . , N) generated from different images are saved in the image storage unit 106, an evaluation value for selecting an optimum mask image can be given, using the same functions f and g as those of equation (8), by:

$$E(n) = \sum_{n=1}^{N} [B2(x, y) f(M_n(x, y), L(x, y)) + B4(x, y) g(M_n(x, y), L(x, y))] \quad (11)$$

At this time, the mask Mn which minimizes the evaluation value E(n) is input to the second inter-image difference processing unit 112.

Furthermore, optimum registration may be performed by performing selection of a mask image and registration. At this time, an evaluation value can be given by:

$$E(i, j, n) = \sum_{n=1}^{N} \sum_{x=smax}^{W-1-smax} \sum_{y=smax}^{H-1-smax} [B2(x, y) f(M_n(x-i-y-j), L(x, y)) + B4(x, y) g(M_n(x-i, y-j), L(x, y))] \quad (12)$$

In equation (12), the mask Mn which minimizes the evaluation value E(i, j, n) and the image registered by the shift amount (i, j) are input to the second inter-image difference processing unit 112.

In this embodiment, registration between the live image and the mask image is performed based on the contrasted vascular region obtained from the first subtraction image and its peripheral pixels. This can reduce a motion artifact especially in the contrasted vascular region of clinical interest.

Second Embodiment

This embodiment will describe a case in which an X-ray image processing apparatus 100 reduces a motion artifact again in an X-ray moving image saved in an image storage unit 106. Assume that the X-ray image processing apparatus 100 saves, in the image storage unit 106, a mask image and an X-ray image obtained by X-ray moving image capturing described in the first embodiment.

The X-ray image processing apparatus 100 can perform change designation of a display frame such as reproduction, pause, frame advance, and frame back of the saved X-ray moving image in accordance with an instruction from the user via the operation unit 107. The X-ray image processing apparatus 100 can change conditions such as a frame number to be used as a mask image in accordance with an instruction from the user via the operation unit 107. Under the changed conditions, the X-ray image processing apparatus 100 inputs, to a mask image generation unit 110, the X-ray image saved in the image storage unit 106. The mask image generation unit 110 generates a mask image M from the input X-ray image under new conditions, and outputs it to the image storage unit 106.

In accordance with a change instruction of the display frame or mask image M from the user via the operation unit 107, the X-ray image processing apparatus 100 updates a DSA image to be displayed. That is, a new frame instructed by the user is set as a live image L, and input to a first inter-image difference processing unit 111 together with the new mask image M.

The first inter-image difference processing unit 111 generates a first subtraction image by subtracting the mask image M from the new live image L, and displays the generated image on a display unit 109. Alternatively, the X-ray image processing apparatus 100 may apply, to the new input, DSA image generation processing described with reference to the flowchart shown in FIG. 2, and display a generated DSA image (second subtraction image) on the display unit 109.

The X-ray image processing apparatus 100 can set a region of interest of the displayed DSA image in accordance with an instruction from the user via the operation unit 107. The instruction from the user may be provided in various methods. In this example, the user designates the coordinates of a pixel by the mouse pointer of the operation unit 107 on the subtraction image displayed on the display unit 109.

Figure 4:
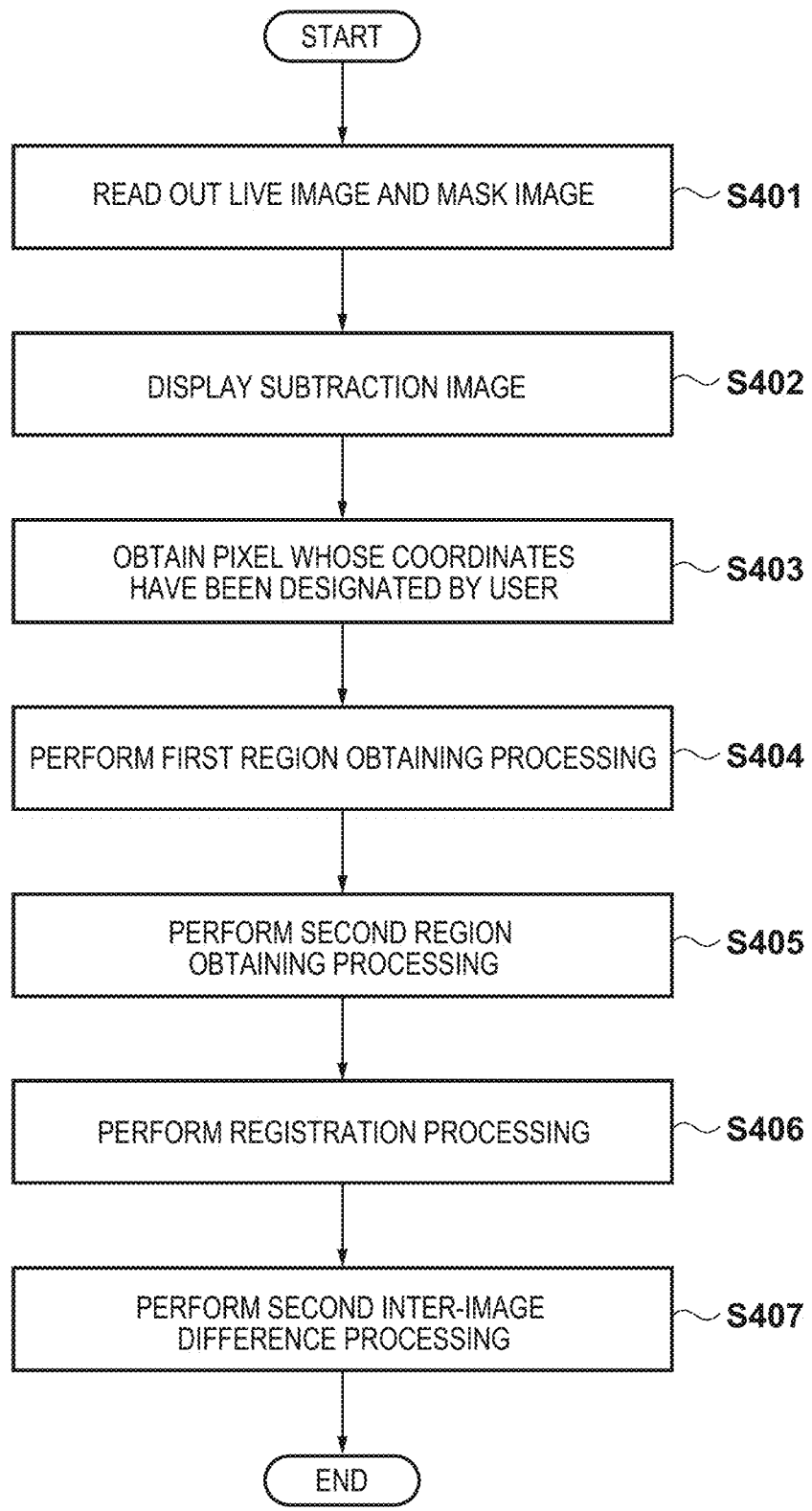
FIG. 4 is a flowchart for explaining a processing procedure according to the second embodiment.

Processing of reducing a motion artifact again in accordance with an instruction from the user via the operation unit 107 will be further described with reference to a flowchart shown in FIG. 4.

In step S401, based on an instruction from the user via the operation unit 107, the X-ray image processing apparatus 100 reads out, from the image storage unit 106, a pair of the live image L and mask image M for generating a subtraction image to reduce a motion artifact again.

In step S402, the X-ray image processing apparatus 100 generates a subtraction image from the readout live image L and mask image M, and displays the generated image on the display unit 109. The subtraction image may be the first subtraction image as the output of the first inter-image difference processing unit 111, or the second subtraction image having undergone the DSA image generation processing shown in FIG. 2, and will simply be referred to as a subtraction image hereinafter.

In step S403, based on an instruction from the user via the operation unit 107, the X-ray image processing apparatus 100 obtains a pixel whose coordinates have been designated in the subtraction image. The pixel whose coordinates are designated is one pixel in a contrasted vascular region of the subtraction image.

In step S404, the X-ray image processing apparatus 100 inputs, to a first region obtaining processing unit 113, the subtraction image and the pixel whose coordinates have been designated, and the first region obtaining processing unit 113 obtains and outputs a contrasted vascular region.

In step S405, the X-ray image processing apparatus 100 inputs, to a second region obtaining processing unit 114, the subtraction image and the contrasted vascular region output from the first region obtaining processing unit 113, and the second region obtaining processing unit 114 obtains and outputs a contrasted vascular peripheral region.

In step S406, the X-ray image processing apparatus 100 inputs, to a registration processing unit 115, the contrasted vascular region, the contrasted vascular peripheral region, and the live image L and mask image M read out in step S401. The registration processing unit 115 obtains a correction amount which minimizes misregistration between pixels (pixel sets) in the live image L and mask image M in the contrast vascular region and contrasted vascular peripheral region, and performs registration between the live image L and the mask image M. As the registration processing, the registration processing unit 115 performs registration between the live image and the mask image with reference to, for example, the mask image. Alternatively, as the registration processing, the registration processing unit 115 performs registration between the live image and the mask image with reference to, for example, the live image. Alternatively, the registration processing unit 115 may deform both the live image and the mask image, and perform registration between the images. For the sake of descriptive simplicity, this embodiment will describe a case in which a registered mask image M'' is obtained by registering the mask image M with the live image L with reference to the live image L, and output from the registration processing unit 115.

In step S407, the X-ray image processing apparatus 100 inputs the set of the live image and registered mask image to a second inter-image difference processing unit 112. The second inter-image difference processing unit 112 generates a third subtraction image by subtracting the registered mask image M' from the live image L, and outputs the generated image.

The X-ray image processing apparatus 100 inputs the third subtraction image as a DSA image to the display unit 109, and the display unit 109 displays the DSA image.

(Obtaining of Contrasted Vascular Region)

Figure 5:
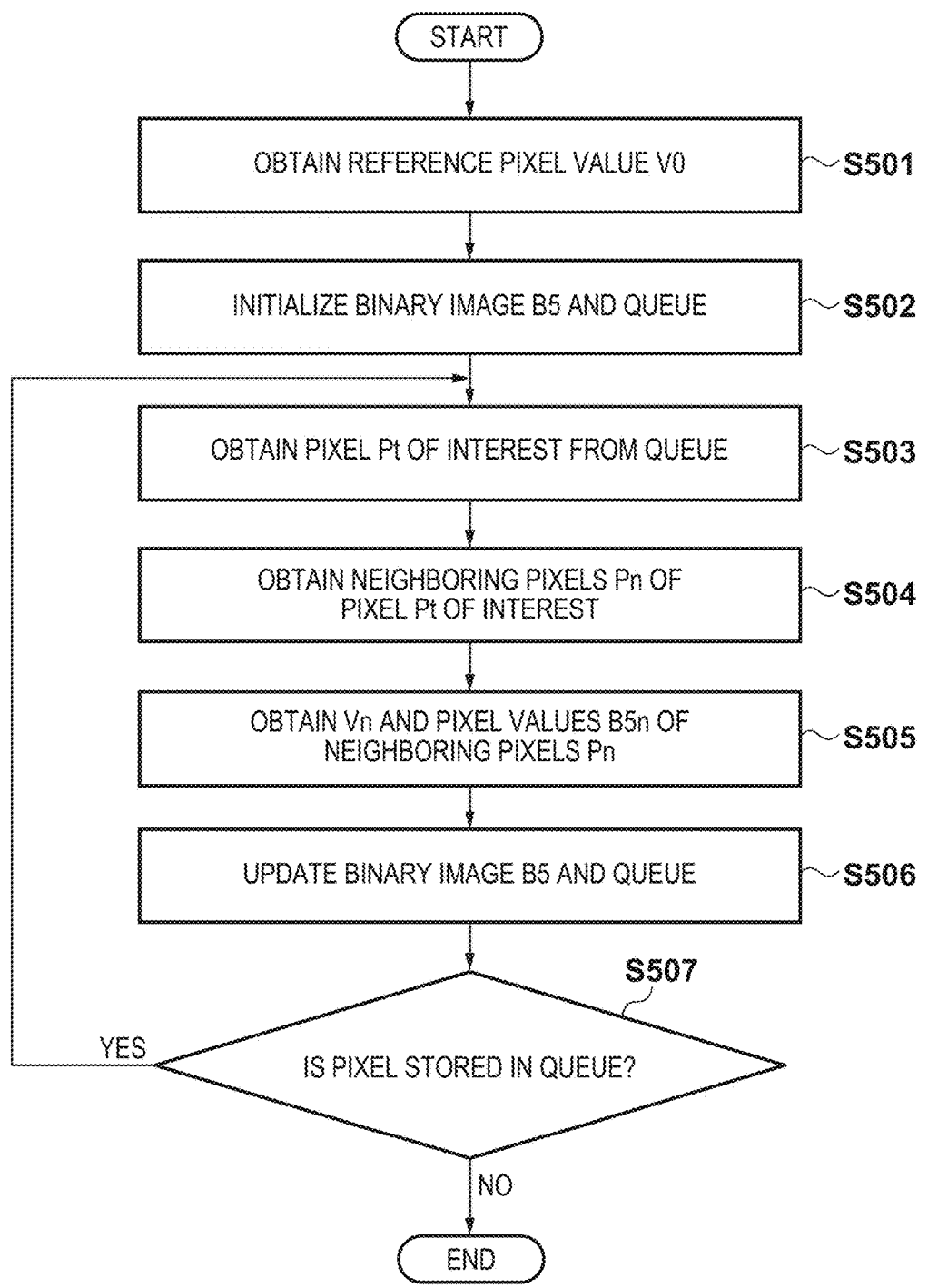
FIG. 5 is a flowchart for explaining the procedure of an example of region obtaining processing according to the second embodiment.

Various methods can be used to obtain the contrasted vascular region based on the coordinates designated by the user in step S404 according to this embodiment. A method of obtaining a binary image B5 as an obtaining target by a region expansion method using, as a start point, a pixel whose coordinates have been designated will be further described with reference to a flowchart shown in FIG. 5. In the binary image B5 as an obtaining target, 1 is set in a contrasted vascular region, and 0 is set in the remaining background region.

In step S501, the first region obtaining processing unit 113 obtains, as a reference pixel value V0, a pixel value S(x0, y0) of a pixel (x0, y0) whose coordinates have been designated in a subtraction image S. The first region obtaining processing unit 113 can directly use the pixel value S(x0, y0) as the reference pixel value V0. The first region obtaining processing unit 113 can also calculate and use the average value of the pixel values of peripheral pixels (x−W, y−W) to (x+W, y+W) of the pixel (x0, y0) in consideration of noise by:

$$V0 = \frac{1}{(W \times 2 + 1)^2} \sum_{j=-W}^{W} \sum_{i=-W}^{W} S(x+i, y+j) \tag{13}$$

In step S502, the first region obtaining processing unit 113 initializes the pixel value of the pixel (x0, y0) to 1 and the remaining background region to 0 in the binary image B5. The first region obtaining processing unit 113 stores the pixel (x0, y0) in a queue serving as a FIFO data structure.

In step S503, the first region obtaining processing unit 113 extracts one pixel from the queue, and sets it as a pixel Pt=(xt, yt) of interest.

In step S504, the first region obtaining processing unit 113 obtains neighboring pixels Pn of the pixel Pt of interest by setting, as a start point, a pixel whose coordinates have been designated. For the sake of descriptive simplicity, the neighboring pixels are four upper, lower, right, and left neighboring pixels Pn (1≤n≤4), that is, P1=(xt, yt−1), P2=(xt, yt+1), P3=(xt−1, yt), and P4=(xt+1, yt).

In step S505, the first region obtaining processing unit 113 obtains pixel values B5n=B5(Pn) on the binary image B5 of the neighboring pixels Pn, and pixel values Vn (the pixel values of pixels on the first difference image) of pixels on the subtraction image S corresponding to the neighboring pixels Pn. The first region obtaining processing unit 113 can directly use the values of the pixels as the pixel values Vn of the subtraction image S, that is, Vn=S(Pn). The first region obtaining processing unit 113 can also use, as the pixel value Vn of the subtraction image S, the average value of the pixel values of the peripheral pixels of the neighboring pixels Pn in consideration of noise in accordance with equation (13).

In step S506, the first region obtaining processing unit 113 updates the value of the binary image B5 based on the values of B5n and Vn (1≤n≤4). For example, the first region obtaining processing unit 113 updates the value of the binary image B5 as given by:

$$B5(Pn) = \begin{cases} 1 & B5n \neq 0, |Vn - V0| \leq Trange \\ 0 & \text{otherwise} \end{cases} \quad (14)$$

where || represents an absolute value symbol, and Trange represents a threshold determined in consideration of capturing conditions and the density of a contrast medium to be used. If equation (14) is used, the value of the binary image B5 is updated from 0 to 1 for a pixel whose pixel value B5n before the update is 0 and for which it is determined that the pixel value Vn has a feature of a contrasted vascular region from which the pixel Pn is to be obtained. Furthermore, the pixel Pn for which the value of the binary image B5 has been updated from 0 to 1 according to equation (14) is newly added to the queue. That is, in this embodiment, if the absolute value of the difference with respect to the reference pixel value V0 obtained in step S501 is equal to or smaller than the predetermined threshold Trange, the first region obtaining processing unit 113 determines that the pixel has a feature of the contrasted vascular region. The first region obtaining processing unit 113 updates the value of the binary image B5, and adds the pixel to the queue.

In step S506, the first region obtaining processing unit 113 determines whether the queue stores a pixel or is empty. If the queue stores a pixel (YES in step S507), the first region obtaining processing unit 113 returns the process to step S503 to repeat the same processes in step S503 and the subsequent steps. If it is determined in step S507 that the queue is empty (NO in step S507), the process ends.

According to the method using the region extension processing, the first region obtaining processing unit 113 obtains a set of pixels which have been connected to a pixel whose coordinates have been designated by the user, and have pixel values considered to be the contrasted vascular region, and outputs it as the binary image B5.

The method using the region extension method which sets, as a start point, one pixel, on an image, whose coordinates have been designated by the user, has been explained above. However, the method of obtaining a contrasted vascular region intended by this embodiment is not limited to this. For example, the user may designate the coordinates of two points as a start point and end point in a contrasted vascular region to be specifically registered, and the first region obtaining processing unit 113 may obtain the contrasted vascular region existing between the two designated points based on these points. More specifically, by limiting a region obtaining target range to a band-shaped region connecting the two points, it is possible to obtain the contrasted vascular region using the region extension method or the above-described method based on the threshold processing and morphological operation.

In this embodiment, since a target is an image obtained by performing image capturing and stored in the image storage unit 106, it is possible to improve the obtaining accuracy of region obtaining processing by reading out temporally preceding and succeeding live images from the image storage unit 106, and using them. More specifically, since a contrasted vascular region does not largely vary in the temporally preceding and succeeding frames of a region obtaining target frame, region obtaining processing which considers that the obtaining results of the respective frames are consecutive between the frames is applicable.

In this embodiment, registration between the live image and the mask image is performed using the contrasted vascular region obtained based on a simple instruction by the user. This can reduce a motion artifact especially in the contrasted vascular region of interest of the user.

Third Embodiment

The respective units shown in FIG. 1 may be implemented by dedicated hardware but the functional components of hardware can be implemented by software. In this case, the functions of the respective units shown in FIG. 1 can be implemented by installing software in an information processing apparatus, and executing the software to implement the image processing method by using the calculation function of the information processing apparatus. By executing the software, for example, preprocessing is performed for each frame of a moving image output from a two-dimensional X-ray sensor 104 to obtain a mask image M and a live image L before and after the inflow of a contrast medium. A subtraction image is obtained in an inter-image difference processing step.

Figure 6:
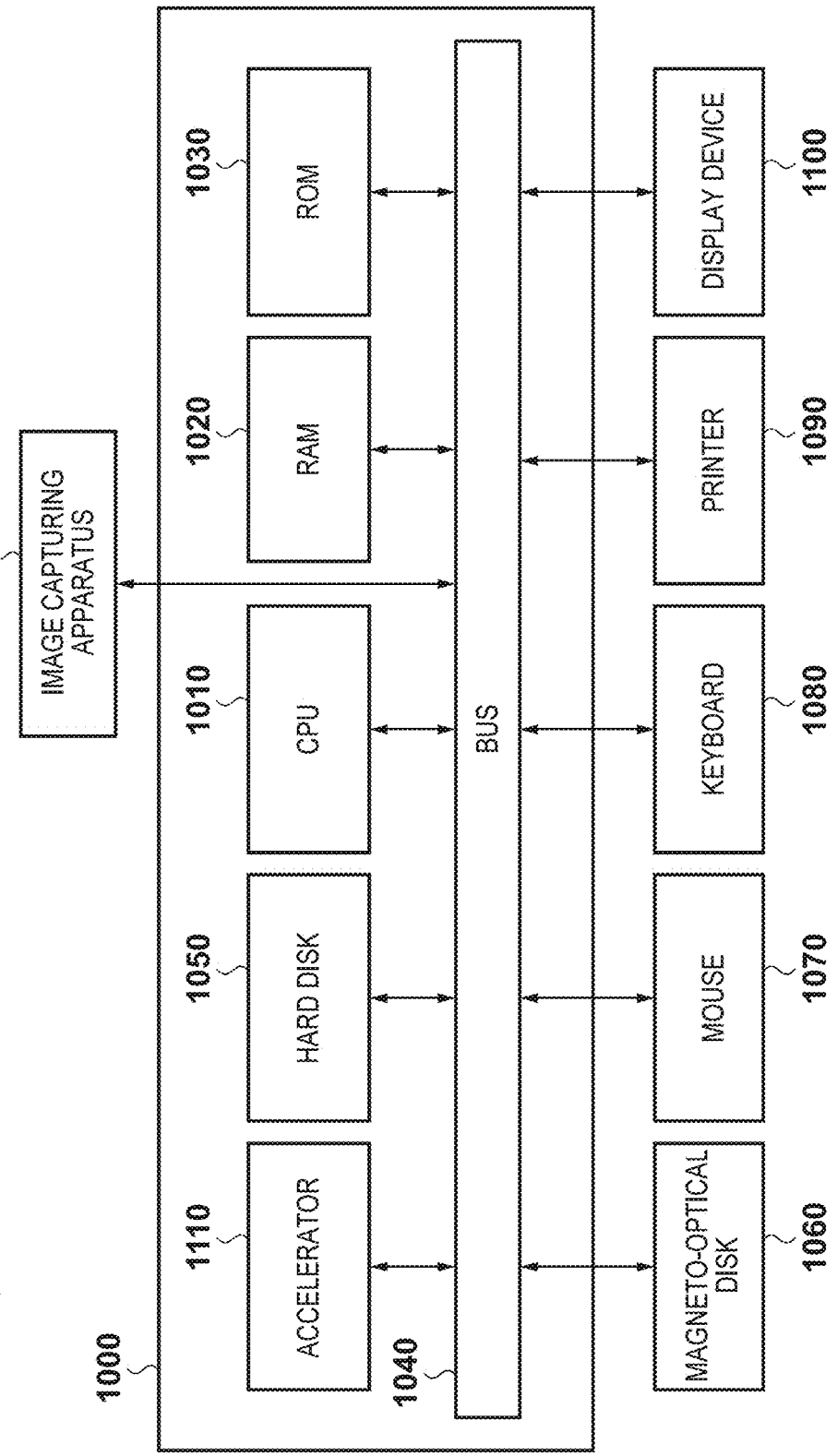
FIG. 6 is a block diagram showing an example of a system using an X-ray image processing apparatus according to an embodiment.

FIG. 6 is a block diagram showing the hardware arrangement of the information processing apparatus and the arrangement of its peripheral devices. An information processing apparatus 1000 is connected to an image capturing apparatus 2000, and can communicate data with it.

A CPU 1010 can control the overall information processing apparatus 1000 by using programs and data stored in a RAM 1020 and ROM 1030, and execute calculation processing regarding predetermined image processing by executing programs.

The RAM 1020 has an area for temporarily storing programs and data loaded from a magneto-optical disk 1060 and hard disk 1050. Furthermore, the RAM 1020 has an area for temporarily storing image data such as a mask image, live image, and subtraction image obtained from the image capturing apparatus 2000. The RAM 1020 also has a work area to be used by the CPU 1010 to execute various processes. The ROM 1030 stores the setting data and boot program of the information processing apparatus 1000 and the like.

The hard disk 1050 holds an OS (Operating System), and programs and data which cause the CPU 1010 of the computer to execute processes to be performed by the respective units shown in FIG. 1. These programs and data are loaded into the RAM 1020 under the control of the CPU 1010, as needed, and processed by the CPU 1010 (computer). Data of a mask image, live image, and subtraction image can also be saved in the hard disk 1050.

The magneto-optical disk 1060 is an example of an information storage medium. Some or all programs or data saved in the hard disk 1050 can be stored in the magneto-optical disk 1060.

A mouse 1070 and a keyboard 1080 can be operated by the operator of the information processing apparatus 1000 to input, to the CPU 1010, various instructions such as designation of the coordinates of a region of interest by an operation unit 107.

A printer 1090 can print out, on a printing medium, an image displayed on a display unit 109. A display device 1100 is formed from a CRT, a liquid crystal screen, or the like, and can display the result of processing by the CPU 1010 as an image, characters, or the like. For example, the display device 1100 can display an image which is processed by the respective units shown in FIG. 1 and is finally output from the display unit 109. In this case, the display unit 109 functions as a display control unit for displaying an image on the display device 1100. A bus 1040 connects the respective units in the information processing apparatus 1000, and can transmit/receive data between them.

(Image Capturing Apparatus 2000)

The image capturing apparatus 2000 will be described next. The image capturing apparatus 2000 can capture a moving image during the inflow of a contrast medium, like an X-ray fluoroscopic apparatus. The image capturing apparatus 2000 transmits the captured image data to the information processing apparatus 1000. Note that a plurality of image data may be transmitted at once to the information processing apparatus 1000, or image data may be transmitted sequentially every time an image is captured.

Other Embodiments

The present invention is also implemented by executing the following processing. That is, software (program) for implementing the functions of the above-described embodiments is supplied to a system or apparatus via a network or various kinds of storage media, and the computer (or CPU or MPU) of the system or apparatus reads out and executes the program.

The present invention is not limited to the above embodiments and various changes and modifications can be made without departing from the spirit and scope of the present invention. Therefore, to apprise the public of the scope of the present invention, the following claims are made.

What is claimed is:

1. An X-ray image processing apparatus comprising:
   a processor; and
   a memory storing a program including instructions executed by the processor,
   the processor and the memory being operatively coupled to function as:
   a difference processing unit configured to generate a first difference image by performing difference processing between a mask image obtained by capturing an object before an inflow of a contrast medium and a live image obtained by capturing the object after the inflow of the contrast medium;
   a first obtaining processing unit configured to obtain a contrasted region indicating a region, into which the contrast medium has flowed, using a distribution of pixel values in the first difference image;
   a second obtaining processing unit configured to obtain a peripheral region of the contrasted region from the first difference image using pixel values of pixels adjacent to the contrasted region; and
   a registration processing unit configured to obtain a correction amount which reduces misregistration between pixels of the live image and the mask image by comparing positions of the contrasted region and the peripheral region, wherein the peripheral region comprises pixels adjacent to the contrasted region, and perform registration between pixels of the live image and the mask image based on the correction amount, wherein
   the difference processing unit generates a second difference image by performing difference processing between the live image and the mask image after performing the registration.

2. The X-ray image processing apparatus according to claim 1, wherein the live image and the mask image used to generate the second difference image are the same images used to generate the first difference image.

3. The X-ray image processing apparatus according to claim 1, wherein the registration processing unit obtains, as a comparison result of the positions, evaluation values of positions obtained from a first degree of contribution corresponding to values of positions of the contrasted region and a second degree of contribution corresponding to values of positions of the peripheral region, and obtains the correction amount, by comparing the evaluation values of the positions, which minimizes misregistration between the pixels of the live image and the mask image, and performs registration between the live image and the mask image using the correction amount.

4. The X-ray image processing apparatus according to claim 3, wherein the registration processing unit obtains, as the correction amount, a pixel shift amount which minimizes an evaluation function having a term indicating a difference in pixel value between the live image and a mask image having undergone pixel shifting, and terms of different weighting coefficients respectively set for the contrasted region and the peripheral region.

5. The X-ray image processing apparatus according to claim 3, wherein the registration processing unit performs registration between the live image and the mask image by shifting positions of corresponding pixels between the live image and the mask image in accordance with the correction amount.

6. The X-ray image processing apparatus according to claim 3, wherein the registration processing unit performs registration between the live image and the mask image by performing image deformation by one of rotation, enlargement, and reduction in accordance with the correction amount.

7. The X-ray image processing apparatus according to claim 3, wherein the registration processing unit performs registration between the live image and the mask image by performing non-rigid body registration processing using a comparison result of the evaluation values of the positions to obtain, as the correction amounts, movement amounts of corresponding positions between the mask image and the live image and a movement amount interpolated between the corresponding positions.

8. The X-ray image processing apparatus according to claim 1, wherein the registration processing unit performs registration between the live image and the mask image by performing edge detection processing for the live image and the mask image, and comparing obtained pieces of edge information.

9. The X-ray image processing apparatus according to claim 3, wherein as registration processing using the correction amount, the registration processing unit performs registration between the live image and the mask image with reference to the mask image.

10. The X-ray image processing apparatus according to claim 3, wherein as registration processing using the correction amount, the registration processing unit performs registration between the live image and the mask image with reference to the live image.

11. The X-ray image processing apparatus according to claim 3, wherein as registration processing using the correction amount, the registration processing unit deforms the live image and the mask image, and performs registration between the live image and the mask image.

12. The X-ray image processing apparatus according to claim 2, wherein the registration processing unit selects one of a plurality of mask images, whose misregistration with respect to the live image is smallest, by comparing positions using the contrasted region and the peripheral region, and the difference processing unit generates the second difference image by performing difference processing between the live image and the selected mask image.

13. The X-ray image processing apparatus according to claim 1, wherein the first obtaining processing unit is implemented using the processor and the memory to function as a calculation unit configured to calculate, as a pixel value of a background region of the first difference image, a pixel value serving as a mode from the distribution of the pixel values in the first difference image, and a threshold processing unit configured to obtain a binary image representing the contrasted region and the peripheral region by threshold processing using the pixel value of the background region as a threshold.

14. The X-ray image processing apparatus according to claim 13, wherein the first obtaining processing unit is implemented using the processor and the memory to further function as an erosion processing unit configured to perform erosion processing of replacing a pixel indicating the contrasted region isolated in the binary image by a pixel indicating the background region.

15. The X-ray image processing apparatus according to claim 14, wherein the first obtaining processing unit is implemented using the processor and the memory to further function as a dilation processing unit configured to perform, for one of the binary image obtained by the threshold processing unit and the binary image having undergone the erosion processing, dilation processing of replacing a pixel indicating the background region adjacent to the contrasted region by a pixel indicating the contrasted region.

16. The X-ray image processing apparatus according to claim 13, wherein the first obtaining processing unit is implemented using the processor and the memory to further function as:

an obtaining unit configured to obtain, as a reference pixel value, a pixel value of a pixel whose coordinates have been designated in the first difference image, an initialization unit configured to initialize pixel values of a binary image to be obtained, an obtaining unit configured to obtain a pixel of interest by setting, as a start point, the pixel whose coordinates have been designated, an obtaining unit configured to obtain neighboring pixels of the pixel of interest, an obtaining unit configured to obtain pixel values of the neighboring pixels on a binary image, and pixel values of pixels on the first difference image corresponding to the neighboring pixels, and an update unit configured to update the pixel values on the binary image using a result of comparing the pixel values of the pixels on the first difference image with the reference pixel value, and the pixel values on the binary image.

17. The X-ray image processing apparatus according to claim 16, wherein the reference pixel value is obtained as an average value of pixel values of peripheral pixels of the pixel whose coordinates have been designated.

18. The X-ray image processing apparatus according to claim 16, wherein the pixel values of the pixels on the first difference image are obtained using an average value of pixel values of peripheral pixels of the neighboring pixels.

19. The X-ray image processing apparatus according to claim 15, wherein the second obtaining processing unit is implemented using the processor and the memory to further function as a second dilation processing unit configured to perform the dilation processing for a binary image output from the dilation processing unit, and a difference processing unit configured to obtain the peripheral region by subtracting the binary image having undergone dilation processing by the dilation processing unit from the binary image having undergone the dilation processing by the second dilation processing.

20. The X-ray image processing apparatus according to claim 3, wherein the processor and the memory are operatively coupled to further function as:

a display unit configured to display one of the first difference image and the second difference image, and a designation unit configured to designate some pixels on the image displayed on the display unit, wherein the first obtaining processing unit obtains the contrasted region using the distribution of the pixel values in the first difference image and the designated pixels, the second processing obtaining unit obtains the peripheral region of the contrasted region from the first difference image using the pixel values of the pixels adjacent to the contrasted region and the pixel values of the designated pixels, the registration processing unit performs registration between pixels of the live image and the mask image by comparing the evaluation values of the positions using the first degree of contribution set to the contrasted region and the second degree of contribution set to the peripheral region, and the difference processing unit generates the second difference image by performing difference processing between the live image and the mask image which have undergone the registration, wherein the live image and the mask image used to generate the second difference image are the same images used to generate the first difference image.

21. The apparatus according to claim 3, wherein the first degree of contribution set to the contrasted region is smaller than the second degree of contribution set to the peripheral region.

22. The apparatus according to claim 3, wherein the registration processing unit obtains the correction amount for the registration so as to minimize the evaluation values of the positions.

23. The apparatus according to claim 3, wherein the registration processing unit performs the registration based on the evaluation values of the positions including a difference in pixel value between the live image and a mask image having undergone pixel shifting.

24. An X-ray image processing method comprising:

a difference processing step of generating a first difference image by performing difference processing between a mask image obtained by capturing an object before an inflow of a contrast medium and a live image obtained by capturing the object after the inflow of the contrast medium;

a first obtaining processing step of obtaining a contrasted region indicating a region, into which the contrast medium has flowed, using a distribution of pixel values in the first difference image;

a second obtaining processing step of obtaining a peripheral region of the contrasted region from the first difference image using pixel values of pixels adjacent to the contrasted region;

a registration processing step of obtaining a correction amount which reduces misregistration between pixels of the live image and the mask image by comparing positions of the contrasted region and the peripheral region, wherein the peripheral region comprises pixels adjacent to the contrasted region, and performing registration between pixels of the live image and the mask image based on the correction amount, and a step of generating a second difference image by performing difference processing between the live image and the mask image after performing the registration.

25. The X-ray image processing method according to claim 24, wherein the live image and the mask image used to generate the second difference image are the same images used to generate the first difference image.

26. A non-transitory computer readable storage medium storing a program for causing a computer to function as each unit of an X-ray image processing apparatus, the apparatus comprising:

a difference processing unit configured to generate a first difference image by performing difference processing between a mask image obtained by capturing an object before an inflow of a contrast medium and a live image obtained by capturing the object after the inflow of the contrast medium;

a first obtaining processing unit configured to obtain a contrasted region indicating a region, into which the contrast medium has flowed, using a distribution of pixel values in the first difference image;

a second obtaining processing unit configured to obtain a peripheral region of the contrasted region from the first difference image using pixel values of pixels adjacent to the contrasted region; and a registration processing unit configured to obtain a correction amount which reduces misregistration between pixels of the live image and the mask image by comparing positions of the contrasted region and the peripheral region, wherein the peripheral region comprises pixels adjacent to the contrasted region, and perform registration between pixels of the live image and the mask image based on the correction amount, wherein the difference processing unit generates a second difference image by performing difference processing between the live image and the mask image after performing the registration.

* * * * *